United States Patent [19]
Ow et al.

[11] Patent Number: 6,114,600
[45] Date of Patent: Sep. 5, 2000

[54] RESOLUTION OF COMPLEX INTEGRATION PATTERNS TO OBTAIN SINGLE COPY TRANSGENES

[75] Inventors: David W. Ow, Hercules; Vibha Srivastava, El Cerrito, both of Calif.

[73] Assignees: The United States of America as represented by the Secretary of Agriculture, Washington, D.C.; The Regents of the University of California, Oakland, Calif.

[21] Appl. No.: 09/175,219

[22] Filed: Oct. 19, 1998

Related U.S. Application Data

[60] Provisional application No. 60/063,886, Oct. 31, 1997.

[51] Int. Cl.$^7$ .............................. C12N 5/04; C12N 5/10; C12N 15/82; C12N 15/87; A01H 5/00
[52] U.S. Cl. ...................... 800/278; 435/69.1; 435/419; 435/469; 435/470; 800/288; 800/292; 800/293; 800/294; 800/298; 800/320; 800/320.3
[58] Field of Search ............................... 435/69.1, 320.1, 435/410, 419, 468, 469, 470; 800/278, 288, 295, 298, 320.3, 292, 293, 294, 320

[56] References Cited

U.S. PATENT DOCUMENTS 5,527,695  6/1996  Hodges et al. ........................ 435/168

OTHER PUBLICATIONS

Sabelli et al, Nucleic Acid Blotting and Hybridisation, In Methods in Plant Biochemistry, vol. 10, J. Bryant, Ed., pp. 79–100, 1993.
V. Srivastava, V. Vasil, and I.K. Vasil, "Molecular Characterization of the Fate of Transgenes in Transformed Wheat (*Triticum aestivum L.*)," Theor Appl Genet 92:1031–1037 (1996).
V.A. Iglesias, E.A. Moscone, I. Papp, F. Neuhuber, S. Michalowski, T. Phelan, S. Spiker, M. Matzke, and A.J.M. Matzke, "Molecular and Cytogenetic Analyses of Stably and Unstably Expressed Transgene Loci in Tobacco," The Plant Cell 9:1251–1264 (Aug. 1997).
M.E. Kononv, B. Bassuner, and S.B. Gelvin, "Integration of T–DNA Binary Vector 'Backbone' Sequences into the Tobacco Genome: Evidence for Multiple Complex Patterns of Integration," The Plant Journal 11:945–957 (1997).
A. Kohli, M. Leech, P. Vain, D.A. Laurie and P. Christou, "Transgene Organization in Rice Engineered Through Direct DNA Transfer Supports a Two–Phase Integration Mechanism Mediated by the Establishment of Integration Hot Spots," Proc. Natl. Acad. Sci. 95:7203–7208 (1998).
J.M. Kooter and J.N.M. Mol, "Trans–Inactivation of Gene Expression in Plants," Curr. Opin. Biotechnol. 4:166–171 (1993).
R.A. Jorgensen, "Cosuppression, Flower Color Patterns, and Metastable Gene Expression States," Science 268:686–691 (1995).
P. Meyer and H. Saedler, "Homology Dependent Gene Silencing in Plants," In *Annual Review of Plant Physiology and Plant Molecular Biology* R.L. Jones, C.R. Somerville and V. Walbot (Eds.) Annual Reviews Inc, Palo Alto, CA, 47:43–48 (1996).

P.D. Cluster, M. O'Dell, M. Metzlaff, and R.B. Flavell, "Details of T–DNA Structural Organization from a Transgenic Petunia Population Exhibiting Co–Suppression," Plant Molecular Biology 32:1197–1203 (1996).
V. Vail, V. Srivastava, A.M. Castillo, M.E. Fromm, and I.K. Vasil, "Rapid Production of Transgenic Wheat Plants By Direct Bombardment of Cultured Immature Embryos," Bio/Technol. 11:1553–1558 (1993).
T.J. Weeks, O.D. Anderson, and A.E. Blechl, "Rapid Production of Multiple Independent Lines of Fertile Transgenic Wheat (*Triticum aestivum*)," Plant Physiology, 102:1077–1084 (1993).
D. Becker, R. Brettschneider, and H. Lorz, "Fertile Transgenic Wheat from Microprojectile Bombardment of Scutellar Tissue," The Plant Journal 5:299–307 (1994).
N.S. Nehra, R.N. Chibbar, N. Leung, K. Caswell, C. Mallard, L. Steinhauer, M. Baga, and K.K. Kartha, "Self–Fertile Transgenic Wheat Plants Regenerated From Isolated Scutellar Tissues Following Microprojectile Bombardment With Two Distinct Gene Constructs," The Plant Journal 5:285–297 (1994).
B. Sauer, "Site–Specific Recombination: Developments and Applications," Curr. Opin. Biotechnol. 5:521–527 (1994).
D.W. Ow, "Recombinase Directed Chromosome Engineering in Plantst," Curr. Opin. Biotechnol. 7:181–186 (1996).
H. Albert, E.C. Dale, E. Lee and D.W. Ow, "Site–Specific Integration of DNA into Wild–Type and Mutant Lox Sites Placed in the Plant Genome," The Plant Journal 7:649–659 (1995).
W.P. Pawlowski and D. Somers, "Transgene Inheritance in Plants Genetically Engineered by Microprojectile Bombardment," Molecular Biotechnology 6:17–30 (1996).
Qin et al, Proc. Natl. Acad. Sci. USA, vol. 91, pp. 1706–1710, 1994.
Medberry et al, Nucl. Acids Res., vol. 23, pp. 485–490, 1995.
Dale et al, Proc. Natl. Acad. Sci. USA, vol. 88, pp. 10558–10562, 1991.
Srivastava, et al, Proc. Natl. Acad. Sci. USA, vol. 96, pp. 11117–11121, 1999.
Kuhstoss et al, J. Mol. Biol., vol. 222, pp. 897–908, 1991.

*Primary Examiner*—Lynette R. F. Smith
*Assistant Examiner*—Ashwin D. Mehta
*Attorney, Agent, or Firm*—M. Howard Silverstein; John D. Fado; Margaret A. Connor

[57] ABSTRACT

The present invention provides methods for producing a transgenic cell having a stably integrated, single copy of an exogenous polynucleotide sequence. The method, which resolves repeated insertions of the introduced polynucleotide sequence into a single copy, involves introducing into a genetic locus of a cell a polynucleotide sequence flanked on each end by a recombination site. The recombination sites are oriented such that contact with a recombinase would not result in deletion of the polynucleotide sequence from the construct. The multiple, tandem copies of the introduced polynucleotide locus are then contacted with a recombinase that catalyzes recombination among the recombination sites. As a result of this method, the multiple, tandem copies are resolved to a single copy.

18 Claims, 4 Drawing Sheets

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence:P1 specific
      primer

<400> SEQUENCE: 1
cagcattgtt catcggtag                                                19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:P2 specific
      primer

<400> SEQUENCE: 2
aggctggcat tatctactcg                                               20

RESOLUTION OF COMPLEX INTEGRATION PATTERNS TO OBTAIN SINGLE COPY TRANSGENES

CROSS-REFERENCE TO RELATED APPLICATIONS

This application claims priority to U.S. Provisional Application Ser. No. 60/063,886, filed Oct. 31, 1997, which application is incorporated herein by reference in its entirety.

BACKGROUND OF THE INVENTION

This invention pertains to the field of genetic engineering. In particular, it relates to the resolution of complex tandem repeats of exogenous polynucleotide sequences into a single copy of a desired exogenous polynucleotide.

Genetic transformation of eukaryotes often results in multiple copies of an exogenous polynucleotide becoming integrated at the same locus. For instance, with current plant transformation methods, the foreign DNA often integrates imprecisely and as multiple copies at a single locus. Often, this results in a long array of transgene copies, not all of which may be full-length or faithful replicas of the introduced DNA (see, e.g. Srivastava, V. et al. *Theoret. Appl. Genet.* 92: 1031–1037 (1996); Kononov, M. E. et al. *Plant J.* 11: 945–957 (1997); Iglesias, V. A. et al. *Plant Cell* 9: 1251–1264 (1997); Kohli, A. et al. *Proc. Natl. Acad. Sci. USA* 95: 7203–7208 (1998)). A tandem array of like-sequences can lead to DNA rearrangements. Homologous recombination can excise or invert endogenous chromosomal DNA found within the array of introduced polynucleotides. The unequal crossing-over between homologous chromosomes or sister chromatids can alter gene copy number.

These structural changes can affect transgene expression, and may be a significant cause of the transgene instability phenomenon; particularly those manifested in subsequent generations (see, e.g., Cluster, P. D. et al. *Plant Mol. Biol.* 32: 1197–1203 (1996)). Aside from structural rearrangements, sufficient correlation has indicated that multiple copies of the transgene, by itself, can induce "homology-dependent gene silencing", where gene expression is repressed due to unknown interactions between homologous sequences (see, Kooter, J. M. and Mol, J. N. M., *Curr. Opinion Biotechnol.* 4: 166–171 (1993); Jorgensen, R. A., *Science* 268: 686–691 (1995); Meyer, P., and Saedler, H., *Annu. Rev. Plant Mol. Biol.* 47: 23–48 (1996); Cluster, P. D. et al., *Plant Mol. Biol.* 32: 1197–1203 (1996)).

For commercial production of a variety of transgenic organisms, the search among transformants for those that have single copy insertions is not only necessary in many cases, but requires a significant effort. For example, in the commercial production of transgenic plants, the prevalence of single copy insertions varies depending on the transformation method and the plant species. With direct DNA transformation methods, such as those reported for the biolistic transformation of wheat, single copy insertions are rarely recovered (see, e.g., Vasil, V. et al., *Bio/Technol.* 11: 1553–1558 (1993); Weeks, T. J. et al., *Plant Physiol.* 102: 1077–1084 (1993); Becker, D. et al., *Plant J.* 5: 299–307 (1994); Nehra, N. S. et al., *Plant J.* 5: 285–297 (1994); Pawlowski, W. and Somers, D., *Mol. Biotechnol.* 6:17–30 (1996)).

Thus, one problem in genetic engineering is the lack of methods to produce transgenic organisms that have only a single copy of a transgene. The invention presented herein addresses this and other problems.

SUMMARY OF THE INVENTION

The present invention provides methods for producing a transgenic cell having a single copy of desired exogenous polynucleotide sequence, rather than tandem, repeated insertions of the introduced polynucleotide sequence. The methods involve introducing into a genetic locus of a cell a polynucleotide sequence flanked on each end by a recombination site for which a recombinase is known. The recombination sites are oriented such that contact with a recombinase would not result in deletion of the polynucleotide sequence from the construct. After integration of the construct, the locus is contacted with a recombinase that catalyzes recombination among the recombination sites. As a result of this method, multiple, tandem copies of the introduced polynucleotide are resolved to a single copy. Single copies of the introduced polynucleotide sequence, however, are not deleted.

In another embodiment, a second pair of recombination sites is used to facilitate removal of a selectable marker or other polynucleotide from the construct after integration. The second pair of recombination sites flank a selectable marker or other polynucleotide to be deleted, and are oriented such that contact with a corresponding recombinase results in deletion of its selectable marker. The recombination sites flanking the selectable marker, which do not recombine with the flanking recombination sites of the construct used to resolve the tandem, repeated insertions, are located in the construct within the first pair of recombination sites.

In some embodiments, the recombinase is introduced into the transgenic cell that comprises the multiple copies of the introduced polynucleotide sequence by introducing into a cell a gene that encodes the recombinase. The recombinase gene can be introduced into a cell by performing a genetic cross between an organism expressing the recombinase gene and an organism that contains the introduced polynucleotide sequence flanked by recombination sites. Alternatively, the recombinase gene can be introduced into the cell simultaneously with the introduction of the introduced polynucleotide sequence comprising the transgene. For instance, the recombinase gene can be present in the introduced polynucleotide sequence. The recombinase gene can be controlled by an inducible promoter or a constitutive promoter.

The invention is useful for obtaining single copy integrated polynucleotides in any cell that is susceptible to integration of exogenous polynucleotides. The cells can be part of a multicellular organism. For instance, the invention is useful for cells of an animal, a plant, or a fungus. The invention is also useful for cells of bacteria and other microorganisms. Typically, the invention will be helpful in genetic engineering of organisms where transformation results in a fraction of the resulting transformants containing tandem, repeated insertions. One example of such organism is a wheat plant.

The invention provides for resolution of tandem repeats within cells that were transformed by any method, including, for example, particle-mediated DNA transfer ("biolistics"), Agrobacterium-mediated transfer, microinjection, electroporation and polyethylene glycol-mediated (PEG) transfer.

Many recombinase systems can be used in the methods of the invention. The recombinase system must be capable of excising the polynucleotides between two recombination sites that are in one orientation while not deleting the intervening polynucleotides if the recombination sites are in a different orientation. A preferred recombinase system is the Cre-lox system. Other systems include the FLP/FRT system, the Gin recombinase system from phage Mu (using a mutant form of the recombinase that can catalyze deletions), and the R/RS system from the pSR1 plasmid.

The invention also provides for the introduction of a second polynucleotide sequence into the cell at the site of integration for the first polynucleotide sequence. In this embodiment, the recombination site from a first introduced polynucleotide sequence recombines with a recombination site present in the second introduced polynucleotide sequence.

BRIEF DESCRIPTION OF THE FIGURES

FIG. 1A is a schematic representation (not to scale) of transformation vectors pVS11, pP2-bar and pP2-cre. Only relevant features and DNA segments (without pUC18 vector backbone) are shown. Symbols: Closed arrowhead, loxP; open arrowhead, lox511. Abbreviations: P1, rice actin promoter; P2, maize ubiquitin promoter; bar, phosphinothricin acetyl transferase coding region followed by a 3' nos terminator; cre, Cre recombinase coding region followed by a 3' nos terminator; E, EcoRI; H, HindIII; P, PstI; X, XhoI. Distances between restriction enzyme sites are indicated in kb.

FIG. 1B is a schematic representation of the resolution product from recombination of lox sites. pVS11 may integrate in multiple copies, with the outermost copies forming four possible configurations (left). Recombination between the outermost lox511 sites (indicated by dashed lines) resolves the complex locus into a unit copy of pVS11 (right). Recombination between loxP sites removes the selectable marker.

FIG. 2A shows a Southern blot demonstrating the excision of the bar gene in F1 progenies. The DNA on the Southern blot in FIG. 2A was cleaved with EcoRI and hybridized to $^{32}$P-labelled bar probe. Genomic DNA of VS10.1 (lane 1), VS10.2 (lane 2), representative F1 progenies of VS10.1×Cre37 (lane 3) and VS10.2×Cre37 (lane 4) are compared with plasmid controls (lane 5) pVS11 (2 kb) and pP2bar (1.4 kb).

FIG. 2B shows an ethidium bromide stained agarose gel containing PCR products from primers corresponding to P1 and P2 sequences. VS10.1 (lane 1) and pVS11 (lane 7) show a 1.8 kb band due to the presence of bar between P1 and P2. Representative F1 progenies of VS10.1×Cre37 (lanes 2–4) show a 0.8 kb band from formation of a new P1-loxP-P2 junction. Neither PCR products are detected from non-transformed control and Cre37 plant (lanes 5, 6, respectively).

FIG. 3A shows a Southern blot that demonstrates reduction of copy number and segregation of a cre-containing locus. HindIII-cleaved genomic DNA was hybridized to a P2 probe. Lanes indicate Cre37, VS10.1 and VS10.2 parents, respective F1 progenies from a cross with Cre37 and the F2 progenies from F1 self-hybridized plants. Molecular size markers range from 2 to 7 kb. Both parents contain an intense ~5 kb band representing internal copies of pVS11. Additional 2.5 kb and 1.5 kb (not shown) bands are detected in the VS10.2 lane which are not found in its F1 progeny. The 4.5 kb band in the F1 lanes represent the cre locus, which contains pP2-bar and pP2-cre. Segregated F2 plants contain the resolved copy of pVS11, indicated by the sole ~7 kb border fragment and the lack of cre and bar bands.

FIG. 3B presents a Southern blot that demonstrates the structure of the resolution product. Genomic DNA of F3 plants was cleaved with PstI and hybridized with P2 DNA (lanes 1–3) or a combination of PstI and XhoI and hybridized with P1 DNA (lanes 4–6). DNA used: lane 1, VS10.1; lane 4, VS10.2; lanes 2 and 5, F3 from VS10.1×Cre37; lanes 3 and 6, F3 from VS10.2×Cre37. Lanes 1–3, 2 kb band corresponds to P2 promoter (see FIG. 1B). Lane 4, the 2 kb band represents P1-bar DNA. F3 progenies of both lines show a 1.4 kb band consistent with the size of the P1 fragment.

FIG. 4A shows a Southern blot demonstrating the unexpected pattern associated with an unresolved locus. Genomic DNA of F2 plants was cleaved with EcoRI and hybridized with bar DNA. A majority of F2 plants shows only the 1.4 kb band derived from pP2-bar of the cre genome (lanes 1–2). However, a few individuals (plants 10.1A–D) show additional bar hybridization bands (lane 3).

FIG. 4B is another Southern blot. Genomic DNA of VS10.1 (lane 1) and F2 progenies of VS10.1×Cre37 (lanes 2–6) were cleaved with HindIII and hybridized with P2 DNA. Most plants lack the 5 kb band (lanes 4–6) indicating excision of internal pVS11 copies. However, a few (plants 10.1A–D) retain the 5 kb band (lanes 2–3), despite the presence of the cre locus (4.5 kb band from the Cre37 genome).

DETAILED DESCRIPTION

Definitions

An "exogenous DNA segment", "heterologous polynucleotide" or a "heterologous nucleic acid", as used herein, is one that originates from a source foreign to the particular host cell, or, if from the same source, is modified from its original form. Thus, a heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

The term "gene" is used broadly to refer to any segment of DNA associated with a biological function. Thus, genes include coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

"Inducible promoter" refers to a promoter that directs expression of a gene where the level of expression is alterable by environmental or developmental factors such as, for example, temperature, pH, transcription factors and chemicals.

The term "isolated", when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest.

The term "purified" denotes that a nucleic acid or protein gives rise to essentially one band in an electrophoretic gel. Particularly, it means that the nucleic acid or protein is at least about 50% pure, more preferably at least about 85% pure, and most preferably at least about 99% pure.

The term "naturally-occurring" is used to describe an object that can be found in nature as distinct from being artificially produced by man. For example, a polypeptide or polynucleotide sequence that is present in an organism (including viruses) that can be isolated from a source in nature and which has not been intentionally modified by man in the laboratory is naturally-occurring.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19: 5081; Ohtsuka et al. (1985) *J. Biol. Chem.* 260: 2605–2608; Cassol et al. (1992); Rossolini et al. (1994) *Mol. Cell. Probes* 8: 91–98). The term nucleic acid is used interchangeably with gene, cDNA, and mRNA encoded by a gene.

"Nucleic acid derived from a gene" refers to a nucleic acid for whose synthesis the gene, or a subsequence thereof, has ultimately served as a template. Thus, an mRNA, a cDNA reverse transcribed from an mRNA, an RNA transcribed from that cDNA, a DNA amplified from the cDNA, an RNA transcribed from the amplified DNA, etc., are all derived from the gene and detection of such derived products is indicative of the presence and/or abundance of the original.

A DNA segment is "operably linked" when placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof.

"Plant" includes whole plants, plant organs (e.g., leaves, stems, roots, etc.), seeds and plant cells and progeny of same. The class of plants that can be used in the methods of the invention is generally as broad as the class of higher plants amenable to transformation techniques, including both monocotyledonous and dicotyledonous plants.

"Promoter" refers to a region of DNA involved in binding the RNA polymerase to initiate transcription.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette" or simply an "expression cassette" is a nucleic acid construct, generated recombinantly or synthetically, with nucleic acid elements that are capable of effecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

"Recombinase" refers to an enzyme that catalyzes recombination between two or more recombination sites. Recombinases useful in the invention catalyze recombination at specific recombination sites which are specific polynucleotide sequences that are recognized by a particular recombinase.

"Transformation rate" refers to the percent of cells that successfully incorporate a heterologous gene into its genome and survive.

The term "transgenic" refers to a cell that includes a specific modification that was introduced into the cell, or an ancestor of the cell. Such modifications can include one or more point mutations, deletions, insertions, or combinations thereof. When referring to an animal, the term "transgenic" means that the animal includes cells that are transgenic. An animal that is composed of both transgenic and non-transgenic cells is referred to herein as a "chimeric" animal.

The term "vector" refers to a composition for transferring a nucleic acid (or nucleic acids) to a host cell. A vector comprises a nucleic acid encoding the nucleic acid to be transferred, and optionally comprises a viral capsid or other materials for facilitating entry of the nucleic acid into the host cell and/or replication of the vector in the host cell (e.g., reverse transcriptase or other enzymes which are packaged within the capsid, or as part of the capsid).

DESCRIPTION OF THE PREFERRED EMBODIMENTS

This invention provides methods for obtaining a cell having a single copy of a transgene. Accordingly, the invention provides methods of resolving multiple copy, complex repeats of exogenous DNA that often result from introduction of exogenous DNA into a cell. The presence of such multiple copy integrated DNA can have adverse effects on the stability and expression of an introduced gene. For example, multiple copies of a transgene can induce "homology-dependent gene silencing" where gene expression is repressed due to unknown interactions between homologous sequences (see, Kooter, J. M. and Mol, J. N. M. *Curr. Opinion Biotechnol.* 4: 166–171 (1993); Jorgensen, R.

A. *Science* 268: 686–691 (1995); Meyer, P., and Saedler, H. *Annu. Rev. Plant Mol. Biol.* 47: 23–48 (1996); Cluster, P. D. et al. *Plant Mol. Biol.* 32: 1197–1203 (1996)). Previously available methods of obtaining single-copy integrants, such as using crossing and screening, are time consuming and labor intensive. The present invention provides methods of resolving multiple, tandem insertions by introducing a construct wherein the exogenous DNA is flanked by a pair of recombination sites for which a specific recombinase is known.

The methods of the invention involve introducing into a cell a construct that has a polynucleotide sequence flanked by a first pair of recombination sites. The recombination sites are oriented such that, if the construct were to be contacted with a corresponding recombinase, the polynucleotide sequence would not be deleted from the construct. For example, when the Cre-lox system is used, the lox sites would be placed in the opposite orientation. Therefore, contacting the construct with the Cre protein would cause inversion of the polynucleotide construct, rather than deletion.

Figure 1:
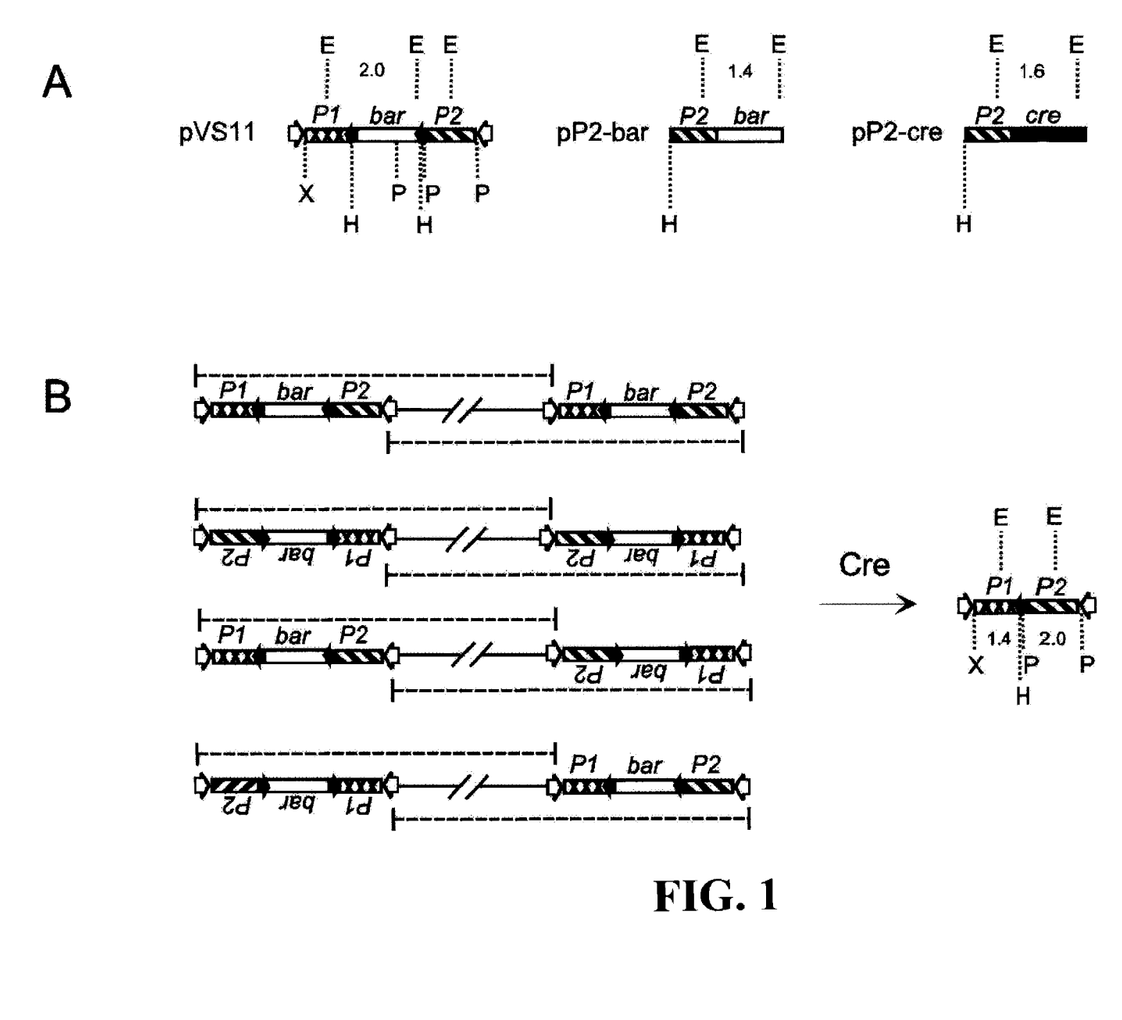

Upon integration of the construct into the chromosome of the cell, the outermost recombination site on one end of the multiple copies of the construct will be in the same orientation as the penultimate recombination site at the other end of the array of integrated constructs (FIG. 1B, left). Accordingly, contact with the recombinase will catalyze deletion of the tandem array between the outermost recombination site on one end of the array and the penultimate recombination site (FIG. 1B, right), resulting in a single copy of the construct remaining integrated. This single copy of the construct is flanked by recombination sites in an orientation that does not lead to excision of the construct when contacted with the recombinase.

If desired, a second exogenous polynucleotide can be targeted to integrate at the site of the first exogenous polynucleotide. The second polynucleotide will contain a recombination site that can recombine with one of the recombination sites that flank the first exogenous polynucleotide.

Recombinases and Recombination Sites

The methods of the invention use recombinase systems to achieve resolution of complex integration events into a single copy insert of a desired exogenous DNA. A recombinase system typically consists of three elements: two specific DNA sequences ("the recombination sites") and a specific enzyme ("the recombinase"). The recombinase catalyzes a recombination reaction between the specific recombination sites.

Recombination sites have an orientation. In other words, they are not palindromes. The orientation of the recombination sites in relation to each other determines what recombination event takes place. The recombination sites may be in two different orientations: parallel (same direction) or opposite. When the recombination sites are in one orientation to each other, then the recombination event catalyzed by the recombinase is an inversion. When the recombination sites are in the other orientation, then any intervening sequence is excised, leaving a single recombination site. The remaining recombination site may or may not be altered, depending on the recombination fidelity of the recombinase.

One recombination system is the Cre-lox system. In the Cre-lox system, the recombination sites are referred to as "lox sites" and the recombinase is referred to as "Cre". When lox sites are in parallel orientation (i.e., in the same direction), then Cre catalyzes a deletion of the intervening polynucleotide sequence. When lox sites are in the opposite orientation, the Cre recombinase catalyzes an inversion of the intervening polynucleotide sequence. This system works in various host cells, including *Saccharomyces cerevisiae* (Sauer, B., *Mol Cell Biol.* 7:2087–2096 (1987)); mammalian cells (Sauer, B. et al., *Proc. Natl Acad. Sci. USA* 85:5166–5170 (1988); Sauer, B. et al., *Nucleic Acids Res.* 17:147–161 (1989)); and plants such as tobacco (Dale, E. et al., *Gene* 91:79–85 (1990)) and Arabidopsis (Osborne, B. et al., *Plant J.* 7(4):687–701 (1995)). Use of the Cre-lox recombinase system in plants is also described in U.S. Pat. No. 5,527,695 and PCT application No. WO 93/01283. Several different lox sites are known, including lox511 (Hoess R. et al., *Nucleic Acids Res.* 14:2287–2300 (1986)), lox66, lox71, lox76, lox75, lox43, lox44 (Albert H. et al., *Plant J.* 7(4): 649–659 (1995)).

Several other recombination systems are also suitable for use in the invention. These include, for example, the FLP/FRT system of yeast (Lyznik, L. A. et al., *Nucleic Acids Res.* 24(19):3784–9 (1996)), the Gin recombinase of phage Mu (Crisona, N. J. et al., *J. Mol. Biol.* 243(3):437–57 (1994)), the Pin recombinase of *E. coli* (see, e.g., Kutsukake K, et. al., *Gene* 34(2–3):343–50 (1985)), the PinB, PinD and PinF from Shigella (Tominaga A et al., *J. Bacteriol.* 173(13):4079–87 (1991)), and the R/RS system of the pSR1 plasmid (Araki, H. et al., *J. Mol. Biol.* 225(1):25–37 (1992)). Thus, recombinase systems are available from a large and increasing number of sources. Recombinase systems may be employed in the cells of any organism that can be transformed with nucleic acids.

The recombinase can be introduced into the cells that contain the multi-copy integrations of exogenous polynucleotides by any method. For example, one can introduce the recombinase in polypeptide form, e.g., by microinjection or other methods. In presently preferred embodiments, however, a gene that encodes the recombinase is introduced into the cells. Expression of the gene results in production of the recombinase, which then catalyzes recombination among the corresponding recombination sites. One can introduce the cre gene into the cell before, after, or simultaneously with, the introduction of the exogenous polynucleotide of interest. In one embodiment, the cre gene is present within the vector that carries the polynucleotide that is to be inserted; the cre gene can even be included within the polynucleotide. In other embodiments, the cre gene is introduced into a transgenic organism, e.g., a transgenic plant, animal, bacteria, fungus, or the like, which is then crossed with an organism that contains the multiple copy integrated exogenous DNA.

Target Organisms

The methods of the invention are useful for obtaining single-copy integrations of exogenous DNA in any type of cell that is susceptible to multiple copy integration events. For example, the methods are useful for cells of animals, plants, fungi, bacteria and other microorganisms. In some embodiments, the cells are part of a multicellular organism, i.e., a transgenic plant or animal. The methods of the invention are particularly useful in situations where transgenic materials are difficult to obtain, such as with transgenic wheat, corn, and animals. In these situations, finding the rare single copy insertion requires the prior attainment of a large number of independently derived transgenic clones, which itself requires great expenditure of effort.

Among the plant targets of particular interest are monocots, including, for example, rice, corn, wheat, rye, barley, bananas, palms, lilies, orchids, and sedges. Dicots are also suitable targets, including, for example, tobacco, apples, potatoes, beets, carrots, willows, elms, maples, roses, buttercups, petunias, phloxes, violets and sunflowers. Other targets include animal and fungal cells. These lists are merely illustrative and not limiting.

Constructs for Introduction of Exogenous DNA into Target Cells

The polynucleotide constructs that are to be introduced into the cells typically include, in addition to the recombination sites, a gene or other functional sequence that will confer a desired phenotype on the cell. Generally, a gene to be expressed will be present in an expression cassette, meaning that the gene is operably linked to expression control signals, e.g., promoters and terminators, that are functional in the host cell of interest. The genes that encode the recombinase and the selectable marker, will also be under the control of such signals that are functional in the host cell. Control of expression is most easily achieved by selection of a promoter. The transcription terminator is not generally as critical and a variety of known elements may be used so long as they are recognized by the cell.

A promoter can be derived from a gene that is under investigation, or can be a heterologous promoter that is obtained from a different gene, or from a different species. Where direct expression of a gene in all tissues of a transgenic plant or other organism is desired, one can use a "constitutive" promoter, which is generally active under most environmental conditions and states of development or cell differentiation. Suitable constitutive promoters for use in plants include, for example, the cauliflower mosaic virus (CaMV) 35S transcription initiation region and region VI promoters, the 1'- or 2'-promoter derived from T-DNA of *Agrobacterium tumefaciens*, and other promoters active in plant cells that are known to those of skill in the art. Other suitable promoters include the full-length transcript promoter from Figwort mosaic virus, actin promoters, histone promoters, tubulin promoters, or the mannopine synthase promoter (MAS). Other constitutive plant promoters include various ubiquitin or polyubiquitin promoters derived from, inter alia, Arabidopsis (Sun and Callis, *Plant J.*, 11(5):1017–1027 (1997)), the mas, Mac or DoubleMac promoters (described in U.S. Pat. No. 5,106,739 and by Comai et al., *Plant Mol. Biol.* 15:373–381 (1990)) and other transcription initiation regions from various plant genes known to those of skill in the art. Such genes include for example, ACT11 from Arabidopsis (Huang et al., *Plant Mol. Biol.* 33:125–139 (1996)), Cat3 from Arabidopsis (GenBank No. U43147, Zhong et al., *Mol. Gen. Genet.* 251:196–203 (1996)), the gene encoding stearoyl-acyl carrier protein desaturase from *Brassica napus* (Genbank No. X74782, Solocombe et al., *Plant Physiol.* 104:1167–1176 (1994)), GPc1 from maize (GenBank No. X15596, Martinez et al., *J. Mol. Biol* 208:551–565 (1989)), and Gpc2 from maize (GenBank No. U45855, Manjunath et al., *Plant Mol. Biol.* 33:97–112 (1997)). Useful promoters for plants also include those obtained from Ti- or Ri-plasmids, from plant cells, plant viruses or other hosts where the promoters are found to be functional in plants. Bacterial promoters that function in plants, and thus are suitable for use in the methods of the invention include the octopine synthetase promoter, the nopaline synthase promoter, and the manopine synthetase promoter. Suitable endogenous plant promoters include the ribulose-1,6-biphosphate (RUBP) carboxylase small subunit (ssu) promoter, the (α-conglycinin promoter, the phaseolin promoter, the ADH promoter, and heat-shock promoters.

Promoters for use in *E. coli* include the T7, trp, or lambda promoters, a ribosome binding site and preferably a transcription termination signal. For eukaryotic cells, the control sequences typically include a promoter which optionally includes an enhancer derived from immunoglobulin genes, SV40, cytomegalovirus, etc., and a polyadenylation sequence, and may include splice donor and acceptor sequences. In yeast, convenient promoters include GAL1-10 (Johnson and Davies (1984) *Mol. Cell. Biol.* 4:1440–1448) ADH2 (Russell et al. (1983) *J. Biol. Chem.* 258:2674–2682), PHO5 (*EMBO J*. (1982) 6:675–680), and MFα (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181–209).

Alternatively, one can use a promoter that directs expression of a gene of interest in a specific tissue or is otherwise under more precise environmental or developmental control. Such promoters are referred to here as "inducible" promoters. Examples of environmental conditions that may effect transcription by inducible promoters include pathogen attack, anaerobic conditions, ethylene or the presence of light. Promoters under developmental control include promoters that initiate transcription only in certain tissues, such as leaves, roots, fruit, seeds, or flowers. The operation of a promoter may also vary depending on its location in the genome. Thus, an inducible promoter may become fully or partially constitutive in certain locations. Inducible promoters are often used to control expression of the recombinase gene, thus allowing one to control the timing of the recombination reaction. Examples of tissue-specific plant promoters under developmental control include promoters that initiate transcription only in certain tissues, such as fruit, seeds, or flowers. The tissue-specific E8 promoter from tomato is particularly useful for directing gene expression so that a desired gene product is located in fruits. See, e.g., Lincoln et al. (1988) *Proc. Nat'l. Acad. Sci. USA* 84: 2793–2797; Deikman et al. (1988) *EMBO J*. 7: 3315–3320; Deikman et al. (1992) *Plant Physiol.* 100: 2013–2017. Other suitable promoters include those from genes encoding embryonic storage proteins. Examples of environmental conditions that may affect transcription by inducible promoters include anaerobic conditions, elevated temperature, or the presence of light. Additional organ-specific, tissue-specific and/or inducible foreign promoters are also known (see, e.g., references cited in Kuhlemeier et al (1987) *Ann. Rev. Plant Physiol.* 38:221), including those 1,5-ribulose bisphosphate carboxylase small subunit genes of *Arabidopsis thaliana* (the "ssu" promoter), which are light-inducible and active only in photosynthetic tissue, anther-specific promoters (EP 344029), and seed-specific promoters of, for example, *Arabidopsis thaliana* (Krebbers et al. (1988) *Plant Physiol.* 87:859). Exemplary green tissue-specific promoters include the maize phosphoenol pyruvate carboxylase (PEPC) promoter, small submit ribulose bis-carboxylase promoters (ssRUBISCO) and the chlorophyll a/b binding protein promoters. The promoter may also be a pith-specific promoter, such as the promoter isolated from a plant TrpA gene as described in International Publication No. W093/07278.

Inducible promoters for other organisms include, for example, the arabinose promoter, the lacZ promoter, the metallothionein promoter, and the heat shock promoter, as well as many others that are known to those of skill in the art.

Typically, constructs to be introduced into these cells are prepared using recombinant expression techniques. Recombinant expression techniques involve the construction of recombinant nucleic acids and the expression of genes in transfected cells. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimnmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

The construction of polynucleotide constructs generally requires the use of vectors able to replicate in bacteria. A plethora of kits are commercially available for the purification of plasmids from bacteria. For their proper use, follow the manufacturer's instructions (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, used to transfect cells or incorporated into *Agrobacterium tumefaciens* to infect and transform plants. Where Agrobacterium is the means of transformation, shuttle vectors are constructed. Cloning in Streptomyces or Bacillus is also possible.

Selectable markers are often incorporated into the polynucleotide constructs and/or into the vectors that are used to introduce the constructs into the target cells. These markers permit the selection of colonies of cells containing the polynucleotide of interest. Often, the vector will have one selectable marker that is functional in, e.g., *E. coli*, or other cells in which the vector is replicated prior to being introduced into the target cell. Examples of selectable markers for *E. coli* include: genes specifying resistance to antibiotics, i.e., ampicillin, tetracycline, kanamycin, erythromycin, or genes conferring other types of selectable enzymatic activities such as β-galactosidase, or the lactose operon. Suitable selectable markers for use in mammalian cells include, for example, the dihydrofolate reductase gene (DHFR), the thymidine kinase gene (TK), or prokaryotic genes conferring drug resistance, gpt (xanthine-guanine phosphoribosyltransferase, which can be selected for with mycophenolic acid; neo (neomycin phosphotransferase), which can be selected for with G418, hygromycin, or puromycin; and DHFR (dihydrofolate reductase), which can be selected for with methotrexate (Mulligan & Berg (1981) *Proc. Nat'l. Acad. Sci. USA* 78: 2072; Southern & Berg (1982) *J. Mol. Appl. Genet.* 1: 327).

Selection markers for plant cells often confer resistance to a biocide or an antibiotic, such as, for example, kanamycin, G 418, bleomycin, hygromycin, or chloramphenicol, or herbicide resistance, such as resistance to chlorsulfuron or Basta. Examples of suitable coding sequences for selectable markers are: the neo gene which codes for the enzyme neomycin phosphotransferase which confers resistance to the antibiotic kanamycin (Beck et al (1982) *Gene* 19:327); the hyg gene, which codes for the enzyme hygromycin phosphotransferase and confers resistance to the antibiotic hygromycin (Gritz and Davies (1983) *Gene* 25:179); and the bar gene (EP 242236) that codes for phosphinothricin acetyl transferase which confers resistance to the herbicidal compounds phosphinothricin and bialaphos.

For some applications, it is desirable to remove a selectable marker or other gene from an exogenous DNA that is introduced into a host cell. Accordingly, the invention provides methods by which such markers can be excised. In these embodiments, the construct that is introduced into the host cell includes, in addition to the pair of recombination sites that flank the polynucleotide of interest, a second pair of recombination sites that flank the selectable marker or other polynucleotide that is to be excised from the construct after integration. The second pair of recombination sites are oriented such that contact with a corresponding recombinase results in deletion of its selectable marker. In the case of the cre/lox system, for example, the lox sites that flank the selectable marker are in the same (parallel) orientation. Thus, contacting the sites with the recombinase results in deletion of the selectable marker. The recombination sites that flank the selectable marker typically do not recombine with the first pair of recombination sites that flank the entire construct. For example, if a pair of loxP recombination sites is positioned on the ends of the construct, one could use a pair of lox511 sites to flank the selectable marker.

One or more additional pairs of recombination sites that do not recombine with the first pair of recombination sites can also be included in the construct for other purposes. For example, a pair of recombination sites can be arranged to flank a promoter fragment in an orientation that results in inversion of the promoter fragment upon contact with the recombinase. For cre/lox, for example, the lox sites are placed in the opposite orientation. If, for example, the promoter fragment is oriented away from a gene to be expressed, contact with the recombinase will cause the promoter fragment to invert so that the promoter can drive expression of the gene.

Methods for Introducing Constructs into Target Cells

The polynucleotide constructs having flanking recombination sites can be introduced into the target cells and/or organisms by any of the several means known to those of skill in the art. For instance, the DNA constructs can be introduced into plant cells, either in culture or in the organs of a plant by a variety of conventional techniques. For example, the DNA constructs can be introduced directly to plant cells using ballistic methods, such as DNA particle bombardment, or the DNA construct can be introduced using techniques such as electroporation and microinjection of plant cell protoplasts. Particle-mediated transformation techniques (also known as "biolistics") are described in Klein et al., *Nature*, 327:70–73 (1987); Vasil, V. etal., *Bio/Technol.* 11:1553–1558 (1993); and Becker, D. et al., *Plant J.*, 5:299–307 (1994). These methods involve penetration of cells by small particles with the nucleic acid either within the matrix of small beads or particles, or on the surface. The biolistic PDS-1000 Gene Gun (Biorad, Hercules, Calif.) uses helium pressure to accelerate DNA-coated gold or tungsten microcarriers toward target cells. The process is applicable to a wide range of tissues and cells from organisms, including plants, bacteria, fungi, algae, intact animal tissues, tissue culture cells, and animal embryos. One can employ electronic pulse delivery, which is essentially a mild electroporation format for live tissues in animals and patients. Zhao, *Advanced Drug Delivery Reviews* 17:257–262 (1995).

Other transformation methods are also known to those of skill in the art. Microinjection techniques are known in the art and well described in the scientific and patent literature. The introduction of DNA constructs using polyethylene glycol (PEG) precipitation is described in Paszkowski et al., *EMBO J.* 3:2717 (1984). Electroporation techniques are described in Fromm et al., *Proc. Natl. Acad. Sci. USA*, 82:5824 (1985). PEG-mediated transformation and electroporation of plant protoplasts are also discussed in Lazzeri, P., *Methods Mol. Biol.* 49:95–106 (1995). Methods are known for introduction and expression of heterologous genes in both monocot and dicot plants. See, e.g., U.S. Pat. Nos. 5,633,446, 5,317,096, 5,689,052, 5,159,135, and 5,679,558; Weising et al. (1988) *Ann. Rev. Genet.* 22:421–477. Transformation of monocots in particular can use various techniques including electroporation (e.g., Shimamoto et al., *Nature* (1992), 338:274–276; biolistics (e.g., European Patent Application 270,356); and Agrobacterium (e.g., Bytebier et al., *Proc. Nat'l Acad. Sci. USA* (1987) 84:5345–5349).

For transformation of plants, DNA constructs may be combined with suitable T-DNA flanking regions and introduced into a conventional *Agrobacterium tumefaciens* host vector. The virulence functions of the *A. tumefaciens* host will direct the insertion of a transgene and adjacent marker gene(s) (if present) into the plant cell DNA when the cell is infected by the bacteria. *Agrobacterium tumefaciens*-meditated transformation techniques are well described in the scientific literature. See, for example, Horsch et al. *Science*, 233:496–498 (1984), Fraley et al., *Proc. Natl. Acad. Sci. USA*, 80:4803 (1983), and Hooykaas, *Plant Mol. Biol.*, 13:327–336 (1989), Bechtold et al., *Comptes Rendus De L Academie Des Sciences Serie Iii-Sciences De La Vie-Life Sciences*, 316:1194–1199 (1993), Valvekens et al., *Proc. Natl. Acad. Sci. USA*, 85:5536–5540 (1988). For a review of gene transfer methods for plant and cell cultures, see, Fisk et al., *Scientia Horticulturae* 55:5–36 (1993) and Potrykus, *CIBA Found. Symp.* 154:198 (1990).

Other methods for delivery of polynucleotide sequences into cells include, for example liposome-based gene delivery (Debs and Zhu (1993) WO 93/24640; Mannino and Gould-Fogerite (1988) *BioTechniques* 6(7): 682–691; Rose U.S. Pat No. 5,279,833; Brigham (1991) WO 91/06309; and Felgner et al. (1987) *Proc. Natl. Acad. Sci. USA* 84: 7413–7414), as well as use of viral vectors (e.g., adenoviral (see, e.g., Berns et al. (1995) *Ann. NY Acad. Sci.* 772: 95–104; Ali et al. (1994) *Gene Ther.* 1: 367–384; and Haddada et al. (1995) *Curr. Top. Microbiol. Immunol.* 199 (Pt 3): 297–306 for review), papillomaviral, retroviral (see, e.g., Buchscher et al. (1992) *J. Virol.* 66(5) 2731–2739; Johann et al. (1992) *J. Virol.* 66 (5):1635–1640 (1992); Sommerfelt et al., (1990) *Virol.* 176:58–59; Wilson et al. (1989) *J. Virol.* 63:2374–2378; Miller et al., *J. Virol.* 65:2220–2224 (1991); Wong-Staal et al., PCT/US94/05700, and Rosenburg and Fauci (1993) in *Fundamental Immunology, Third Edition* Paul (ed) Raven Press, Ltd., New York and the references therein, and Yu et al., *Gene Therapy* (1994) supra.), and adeno-associated viral vectors (see, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351 and Samulski (supra) for an overview of AAV vectors; see also, Lebkowski, U.S. Pat. No. 5,173, 414; Tratschin et al. (1985) *Mol. Cell. Biol.* 5(11):3251–3260; Tratschin et al. (1984) *Mol. Cell. Biol.*, 4:2072–2081; Hermonat and Muzyczka (1984) *Proc. Natl. Acad. Sci. USA*, 81:6466–6470; McLaughlin et al. (1988) and Samulski et al. (1989) *J. Virol.*, 63:03822–3828), and the like.

Methods by which one can analyze the integration pattern of the introduced exogenous DNA are well known to those of skill in the art. For example, one can extract DNA from the transformed cells, digest the DNA with one or more restriction enzymes, and hybridize to a labeled fragment of the polynucleotide construct. The inserted sequence can also be identified using the polymerase chain reaction (PCR). See, e.g., Sambrook et al., *Molecular Cloning-A Laboratory Manual*, Cold Spring Harbor Laboratory, Cold Spring Harbor, N.Y., 1989 for descriptions of these and other suitable methods.

Regeneration of Transgenic Plants and Animals

The methods of the invention are particularly useful for obtaining transgenic and chimeric multicellular organisms that have a single copy of a desired exogenous polynucleotide. Methods for obtaining transgenic and chimeric organisms, both plants and animals, are well known to those of skill in the art.

Transformed plant cells, derived by any of the above transformation techniques, can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124–176, Macmillian Publishing Company, New York (1983); and in Binding, *Regeneration of Plants, Plant Protoplasts*, pp. 21–73, CRC Press, Boca Raton, (1985). Regeneration can also be obtained from plant callus, explants, somatic embryos (Dandekar et al., *J. Tissue Cult. Meth.*, 12:145 (1989); McGranahan et al., *Plant Cell Rep.*, 8:512 (1990)), organs, or parts thereof. Such regeneration techniques are described generally in Klee et al., *Ann. Rev. of Plant Phys.*, 38:467–486 (1987).

The methods are useful for producing transgenic and chimeric animals of most vertebrate species. Such species include, but are not limited to, nonhuman mammals, including rodents such as mice and rats, rabbits, ovines such as sheep and goats, porcines such as pigs, and bovines such as cattle and buffalo. Methods of obtaining transgenic animals are described in, for example, Puhler, A., Ed., *Genetic Engineering of Animals*, VCH Publ., 1993; Murphy and Carter, Eds., *Transgenesis Techniques: Principles and Protocols* (*Methods in Molecular Biology*, Vol. 18), 1993; and Pinkert, CA, Ed., *Transgenic Animal Technology: A Laboratory Handbook*, Academic Press, 1994. Transgenic fish having specific genetic modifications can also be made using the claimed methods. See, e.g., Iyengar et al. (1996) *Transgenic Res.* 5: 147–166 for general methods of making transgenic fish.

One method of obtaining a transgenic or chimeric animal having specific modifications in its genome is to contact fertilized oocytes with a vector that includes the polynucleotide of interest flanked by recombination sites. For some animals, such as mice fertilization is performed in vivo and fertilized ova are surgically removed. In other animals, particularly bovines, it is preferably to remove ova from live or slaughterhouse animals and fertilize the ova in vitro. See DeBoer et al., WO 91/08216. In vitro fertilization permits the modifications to be introduced into substantially synchronous cells. Fertilized oocytes are then cultured in vitro until a pre-implantation embryo is obtained containing about 16–150 cells. The 16–32 cell stage of an embryo is described as a morula. Pre-implantation embryos containing more than 32 cells are termed blastocysts. These embryos show the development of a blastocoel cavity, typically at the 64 cell stage. If desired, the presence of a desired exogenous polynucleotide in the embryo cells can be detected by methods known to those of skill in the art. Methods for culturing fertilized oocytes to the pre-implantation stage are described by Gordon et al. (1984) *Methods Enzymol.* 101: 414; Hogan et al. *Manipulation of the Mouse Embryo: A Laboratory Manual*, C.S.H.L. N.Y. (1986) (mouse embryo); Hammer et al. (1985) *Nature* 315: 680 (rabbit and porcine embryos); Gandolfi et al. (1987) *J. Reprod. Fert.* 81: 23–28; Rexroad et al. (1988) *J. Anim. Sci.* 66: 947–953 (ovine embryos) and Eyestone et al. (1989) *J. Reprod. Fert.* 85: 715–720; Camous et al. (1984) *J. Reprod. Fert.* 72: 779–785; and Heyman et al. (1987) *Theriogenology* 27: 5968 (bovine embryos). Sometimes pre-implantation embryos are stored frozen for a period pending implantation. Pre-implantation embryos are transferred to an appropriate female resulting in the birth of a transgenic or chimeric animal depending upon the stage of development when the transgene is integrated. Chimeric mammals can be bred to form true germline transgenic animals.

Alternatively, the methods can be used to obtain embryonic stem cells (ES) that have a single copy of the desired exogenous polynucleotide. These cells are obtained from preimplantation embryos cultured in vitro. See, e.g., Hooper, ML, *Embryonal Stem Cells: Introducing Planned Changes into the Animal Germline* (Modern Genetics, v. 1), Int'l. Pub. Distrib., Inc., 1993; Bradley et al. (1984) *Nature* 309, 255–258. Transformed ES cells are combined with blastocysts from a non-human animal. The ES cells colonize the embryo and in some embryos form the germ line of the resulting chimeric animal. See Jaenisch, *Science*, 240: 1468–1474 (1988). Alternatively, ES cells or somatic cells that can reconstitute an organism ("somatic repopulating cells") can be used as a source of nuclei for transplantation into an enucleated fertilized oocyte giving rise to a transgenic mammal. See, e.g., Wilmut et al. (1997) *Nature* 385: 810–813.

EXAMPLES

The following example is offered to illustrate, but not to limit the present invention.

Example 1

Generation of pVS11 transformants. Plasmid pVS11 was delivered into wheat immature embryos through particle bombardment and cultures were selected on bialaphos. From a single experiment on approximately 900 immature embryos, 11 putative transgenic plants were regenerated from resistant calli. T1 progeny from these lines were germinated on selection but only 2 lines, VS10.1 and VS10.2, yielded resistant seedlings. With both lines, a 3:1 segregation for bialaphos resistance was observed, indicating a single integration locus. Southern analysis using bar DNA as a probe detected the presence of bar DNA in VS10.1 and VS10.2, but not in the other 9 lines.

Generation of cre expressing lines. Cre recombinase was introduced into the system by crossing a wheat plant expressing cre into the wheat plant transformed with pVS11. The cre-expressing line was obtained by particle bombardment of wheat embryos with pP2-cre and pP2-bar DNA. Both constructs use the maize ubiquitin promoter (P2) to drive expression of cre or bar (FIG. 1A). Putative transformants were transferred to the greenhouse and T1 embryos germinated on bialaphos-containing media. Embryos of four transgenic lines (Cre 34, 35, 37, 39) were assayed for Cre activity through bombardment with pHK52, which contains promoter P2 transcribing an antisense gus coding sequence. Since the gus gene is flanked by oppositely oriented loxP sites, Cre-mediated recombination is expected to invert the gus fragment and permit expression of sense strand mRNA. The T1 embryos of Cre34 and Cre37 lines stained blue after bombardment with pHK52, whereas the other lines, as well as non-transgenic control embryos, failed to show blue staining. Based on this assay, we considered Cre37 to be the stronger expressing line. The presence of bar and cre DNA in Cre37 was confirmed by Southern hybridization.

Figure 2:
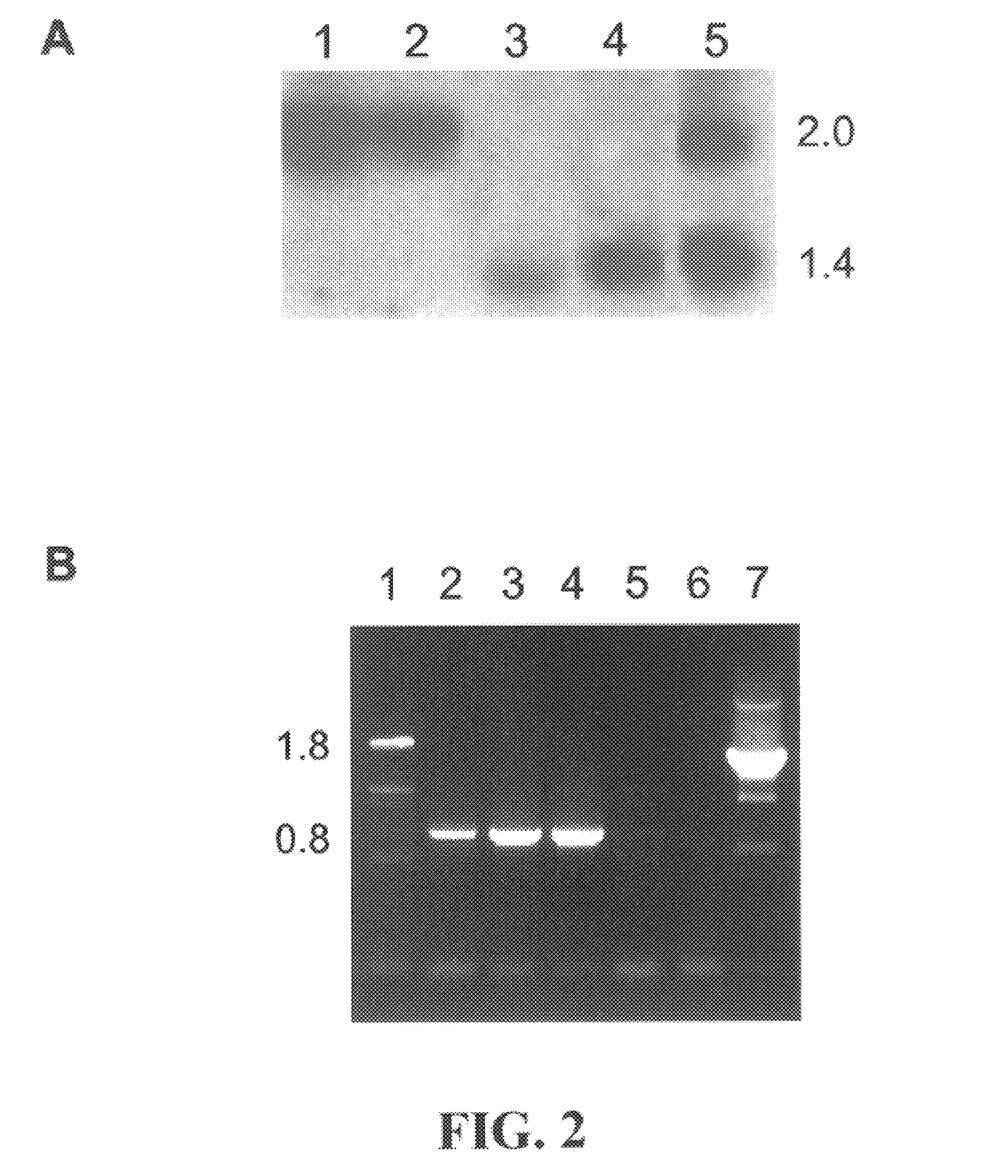

Marker gene excision in F1 progeny. Ten T2 plants derived from each of VS10.1 and VS10.2 were crossed as both the male and female donors to a homozygous Cre3 7 plant. The F1 seeds of each cross were germinated on bialaphos and plants were grown in the greenhouse for molecular analyses. Each of the parental Cre37, VS10.1 and VS10.2 lines contains the bar gene as a selectable marker. Genomic DNA of the parents and their F1 plants were cleaved with EcoRI and hybridized with bar DNA. The Cre37 parent has an internal 1.4 kb EcoRI fragment corresponding to P2-bar while the VS10.1 and VS10.2 parents have an internal 2 kb EcoRI band corresponding to P1-bar (FIG. 1A). In the F1 plants, a 1.4 kb band was detected which corresponds to the P2-bar of the Cre37 genome while the 2 kb P1-bar band from pVS11 was not found (FIG. 2A, lanes 3–4). This would be consistent with Cre-loxP mediated excision of the bar gene from the VS10.1 and VS10.2 genomes. This excision should fuse P1 and P2 sequences linked by a single loxP site. The presence of this new junction in the F1 plants was detected by PCR analysis (FIG. 2B). Using primers corresponding to P1 and P2 sequences, a band of 1.8 kb representing the P1-loxP-bar-loxP-P2 linkage was amplified from VS10.1 and VS10.2 DNA, but not from the progenies of the VS10.1×Cre37 and VS10.2× Cre37 crosses. Instead, a new 0.8 kb fragment corresponding to the new P1-loxP-P2 junction was detected. This 0.8 kb fragment contains a functional loxP site as this PCR product could recombine with a plasmid substrate in an in vitro recombination reaction. The nucleotide sequence of this PCR fragment confirmed that a precise P1 -loxP-P2 junction was formed (data not shown).

Figure 3:
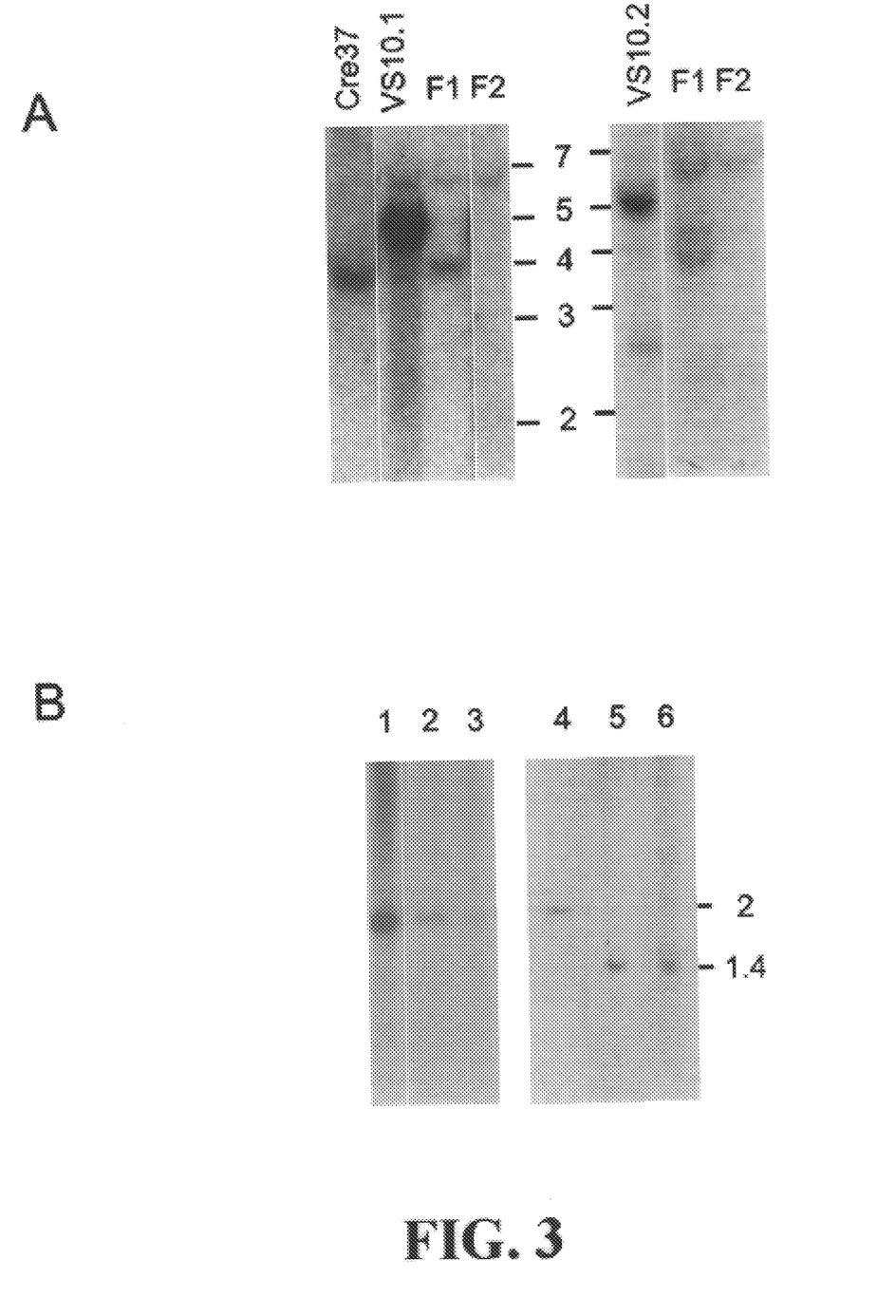

Reduction of copy number in F1 plants. Genomic DNA of VS10.1 and VS10.2 parents and their F1 progenies were cleaved with HindIII just outside of the loxP flanked bar gene in pVS11 and hybridized with P2 DNA (FIG. 3A). The VS10.1 and VS10.2 parents show an intense ~5 kb band that represents multiple copies of pVS11 DNA. A faint band of ~7 kb represents the border fragment (P2-lox511-host DNA). The border fragments of the two parents are not the same. When cleaved with BamHI, the same P2 probe reveals a 6 kb and a 8 kb border band for lines VS10.1 and VS10.2, respectively (data not shown). Two closely located bands of more than 5 kb can be discerned in a lighter exposure of the VS10.1 lane, indicating that the integration pattern is not simply a repetition of tandem direct or inverted copies. In VS 10.2, a lower transgene copy number, along with ~2.5 kb and ~1.5 kb bands, are observed. These unexpected band sizes could represent a complex pattern of transgene integration that includes truncated copies. In contrast to the parents, F1 progenies of both lines were found to have the border copy, but without the internal bands. Since P2 was the hybridization probe, the 4.5 kb band in the F1 lanes represents cre genome DNA. When HindIII cleaved Cre37 DNA was probed with bar or cre DNA, it was found that the 4.5 kb band corresponds to co-migrating P2-cre and P2-bar DNA (data not shown).

Transmission of single copy transgene to F2 progeny. Segregation of the pVS11 integration locus from bar and cre DNA was determined in the F2 progeny of self-fertilized F1 plants. Genomic DNA of 40 F2 plants of VS10.1×Cre37 and 18 F2 plants of VS10.2×Cre37 were cleaved with EcoRI and hybridized with bar and cre probes. As expected, some of the F2 progenies showed the presence of the 1.6 kb P2-cre fragment, whereas others lacked this band (data not shown). When probed with bar DNA, a few lacked the 1.4 kb P2-bar fragment, but surprisingly, a majority retained this DNA. This suggests that the 1.6 kb P2-cre and 1.4 kb P2-bar fragments in the Cre37 genome do not necessarily co-segregate.

Twenty randomly selected F2 plants from VS10.1×Cre37 and all 18 of the F2 plants of VS10.2×Cre37 were analyzed for pVS11 copy number using P2 to probe HindIII cleaved DNA. Surprisingly, only 16 of 20 VS10.1×Cre37 F2 plants and 12 of 18 VS10.2×Cre37 F2 plants showed single copy insertion of the introduced pVS11 DNA. The others were found to have retained more than a single copy. Therefore, although Southern analysis of the F1 parents showed complete resolution of the integration loci, at least when leaf tissues were analyzed, germline cells must have been chimeric. Of the 16 F2 plants of VS10.1×Cre37 that showed single copy insertion, 4 of them had segregated away the cre and bar genes, as the P2 probe failed to detect the 4.5 kb P2-bar/P2-cre comigrating band (FIG. 3A). Similarly, 2 out of 12 single copy VS10.2×Cre37 F2 plants were found to lack cre and bar genes. These 6 F2 plants were selected for further analysis. They were probed with the ampicillin resistance gene (amp) that is part of the "vector backbone" of the three plasmids pVS11, pP2-cre and pP2-bar. The Southern blot showed that these six F2 plants lacked the amp marker (data not shown). In contrast, the parents VS10.1 and VS10.2, as well as plants that have retained the cre locus, all showed hybridization to the amp probe. In these 6 F2 progenies, all copies of the pVS11-derived amp gene must have laid internal to the outermost lox sites and were therefore removed by the Cre-lox reaction.

Target site integrity in F3 progeny. From a backcross to the wild type (non-transgenic) parent, F3 progenies hemizygous for the transgenic target site were obtained from the 4 VS10.1×Cre37 and the 2 VS10.2×Cre37 lines that lack the P2-cre, P2-bar, and amp fragments. To determine if the single copy target site contains the expected fragment sizes, genomic DNA of these F3 plants were cleaved with PstI and probed with P2 DNA (FIG. 3B). A 2 kb fragment was observed which is consistent with a full-length P2 promoter (FIG. 1B). This same size fragment was also observed in the VS10 parents. When the F3 progeny DNA was cleaved with XhoI and PstI and then probed with PI DNA, a 1.4 kb band representing the full-length P1 fragment was found. In contrast, the parents showed a 2 kb fragment as the bar gene, downstream of P1, harbors a Pst1 site (FIGS. 1A, 3B). The data indicate that both promoters in the 6 F3 plants are intact, consistent with the intended structure depicted in FIG. 1B.

Figure 4:
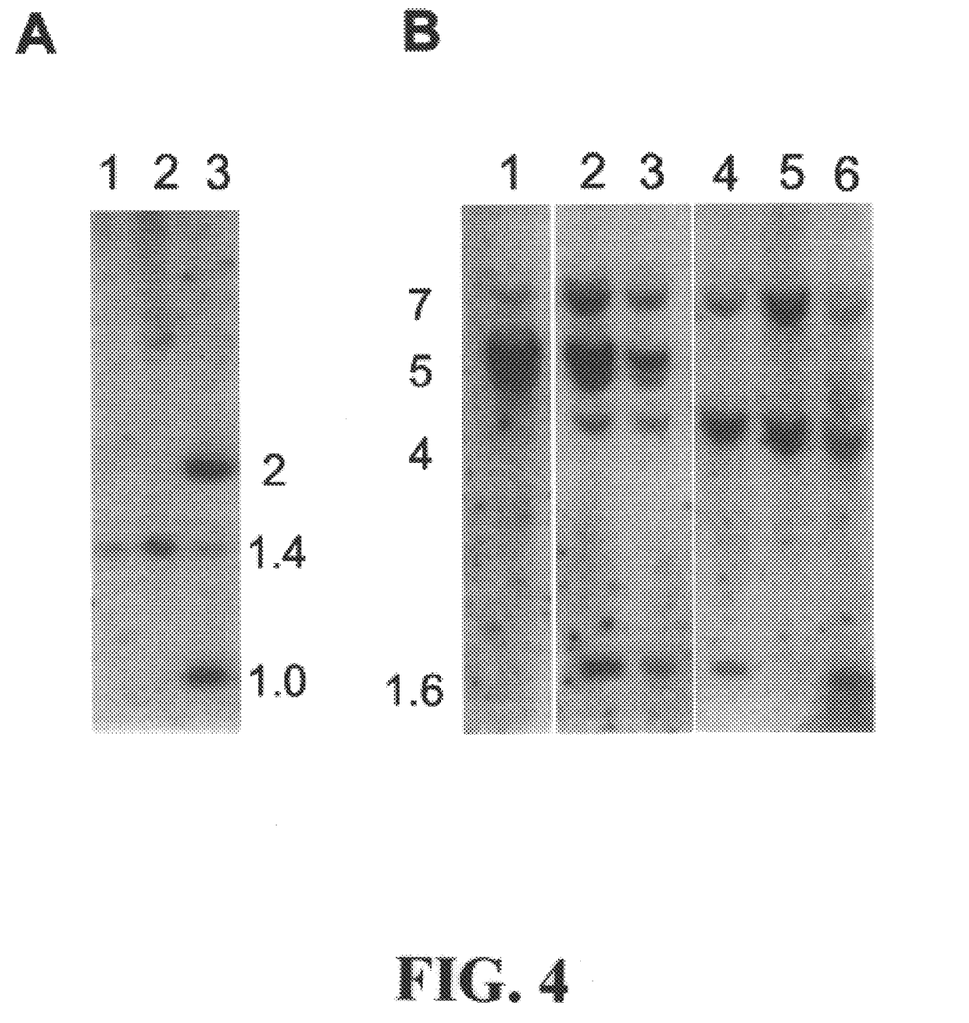

Rare instances of an unexpected pattern. Although the majority of the F2 progenies showed hybridization patterns that correspond to interpretation, an unexpected band was found in 4 out of the 40 F2 plants derived from a single F1 parent of the VS10.1×Cre37 cross. In these individuals, plants 10.1A,B,C and D, the bar probe detected 3 EcoRI bands of sizes 2.0, 1.4 kb and 1.0 kb (FIG. 4A, lane 3). The, 1.4 kb and 2.0 kb fragments correspond, respectively, to P2-bar from the Cre37 genome, and P1-bar of the unresolved pVS11 integration locus. Incomplete excision is consistent with the detection of multiple copies of pVS11 DNA. When HindIII cleaved 10.1A and 10.1B genomic DNA was probed with P2 DNA, the 5 kb fragment characteristic of the unresolved locus was observed (FIG. 4B, lanes 2–3). The presence of the 1.0 kb bar band, however, is beyond interpretation (FIG. 4A, lane 3). One possibility may be that a few copies of the circular loxP-bar DNA had excised from the pVS11 locus but had persisted, perhaps even integrating elsewhere in multiple copies.

Experimental Protocol

Transformation Vectors. Plasmids were constructed by standard recombinant DNA methods. Plasmid pVS11 (7 kb) contains a fragment flanked by synthetic lox511 sites of opposite orientation in pUC18 backbone. The fragment contains a bar coding region flanked by synthetic loxP sites. Upstream and downstream of bar are the rice actin promoter (P1) (McElroy, D. et al., *Mol. Gen. Genet.* 231: 150–160 (1993)) and the maize ubiquitin promoter (P2) (Christensen, A. H. et al., *Plant Mol. Biol.* 18: 675–689 (1992), respectively. Although not relevant to this report, a FRT site (FLP-FRT recombination system) is inserted upstream of P1 (not shown in the figures), intended for use in future gene targeting experiments.

Wheat Transformation. Spring wheat var. Bobwhite was grown in the greenhouse and immature embryos collected for transformation using the particle bombardment method (Vasil, V. et al., *Bio/Technol.* 11:1553–1558 (1993)). Bombarded embryos were cultured and selected in the presence of bialaphos (3 mg/L). Putative transformants were grown in a greenhouse for analyses. For selection of pP2-cre, an equivalent amount of pP2-bar DNA was used for co-transformation. Cre activity in pP2-cre transformed plants was determined by bombarding T1 embryos with pHK52, which exhibits GUS activity upon Cre-mediated inversion of the gus coding region. The embryos were stained for GUS activity 48 hours after bombardment.

Molecular analyses. Wheat genomic DNA (10 µg), isolated using the CTAB method, was subjected to Southern hybridization with $^{32}$P labeled DNA probes. Recombination junctions in the wheat genome were detected by PCR analysis using primers specific to P1 (5' CAGCATTGT-TCATCGGTAG 3', SEQ ID NO: 1) and P2 (5'AGGCTGGCATTATCTACTCG 3', SEQ ID NO:2) specific primers. Intermolecular Cre-lox recombination reactions between PCR-derived junctions and lox-containing DNA fragments were conducted in vitro as described previously (Albert, H. et al., *Plant J.* 7: 649–659 (1995)). DNA sequencing of PCR fragments was carried out using the ABI Prism automated sequencing system.

It is understood that the example and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of resolving multiple copies of a construct integrated at a locus in a plant cell to a single copy of said construct at said locus, the method comprising:

introducing into the cell a construct comprising an exogenous polynucleotide sequence flank by a first pair of recombination sites oriented such that contact with a recombinase would not result in deletion of the polynucleotide sequence from the construct to obtain a cell which comprises multiple copies of the construct integrated at a locus of a cell chromosome; and contacting the locus with a recombinase that catalyzes recombination among the recombination sites of the multiple copies at said locus;

wherein the recombination results in resolution of the multiple copies of the introduced construct into a single copy of the construct integrated at said locus.

2. The method of claim 1, wherein the first pair of recombination sites are oriented in the opposite orientation.

3. The method of claim 1, wherein the recombinase is a Cre polypeptide and the recombination sites are lox sites.

4. The method of claim 1, wherein the recombinase and recombination sites are selected from the group consisting of FLP/FRT, and R/RS.

5. The method of claim 1, wherein a selectable marker is located between the first pair of recombination sites.

6. The method of claim 5, wherein said selectable marker is flanked by a second pair of recombination sites, wherein the second pair of recombination sites do not recombine with the first pair of recombination sites and are oriented such that said contacting with said recombinase results in deletion of said selectable marker and one of said second pair of recombination sites from the construct such that said construct integrated at said locus comprises said exogenous polynucleotide flanked by said first pair of recombination sites and the other of said second pair of recombination sites.

7. The method of claim 6, wherein the first pair of recombination sites and the second pair of recombination sites are different species of lox sites.

8. The method of claim 1, wherein the recombinase is encoded by a recombinase gene which is present in the cell.

9. The method of claim 8, wherein the recombinase gene is under the control of an inducible promoter.

10. The method of claim 8, wherein the recombinase gene is introduced into the cell which comprises multiple copies of the introduced construct by crossing with a cell which comprises the recombinase gene.

11. The method of claim 8, wherein the recombinase gene is introduced into the cell simultaneously with the introduction of the introduced construct comprising the exogenous polynucleotide sequence.

12. The method of claim 11, wherein the recombinase gene is present on a polynucleotide which comprises the introduced construct comprising the exogenous polynucleotide sequence.

13. The method of claim 1, wherein the cell comprises a multicellular organism.

14. The method of claim 13, wherein the multicellular organism is a plant.

15. The method of claim 14, wherein the plant is a monocot.

16. The method of claim 15, wherein the monocot is a wheat plant.

17. The method of claim 1, wherein the introduced construct is introduced into the cell by a method selected from the group consisting of particle-mediated DNA transfer, Agrobacterium-mediated transfer, microinjection, electroporation and polyethylene glycol-mediated (PEG) transfer.

18. The method of claim 1, wherein the method further comprises introducing into the cell a second exogenous polynucleotide sequence which comprises a second polynucleotide sequence and a recombination site, wherein the recombination site can recombine with a previously introduced recombination site, resulting in integration of the second polynucleotide sequence at the previously introduced recombination site.

* * * * *